US008389695B2

(12) United States Patent
Kunstelj et al.

(10) Patent No.: US 8,389,695 B2
(45) Date of Patent: Mar. 5, 2013

(54) SELENIUM CONTAINING MODIFYING AGENTS AND CONJUGATES

(75) Inventors: Menci Kunstelj, Skofja Loka (SI); Viktor Menart, Logatec (SI); Veronika Verbic, legal representative, Logatec (SI); Gabriela Ambrozic, Ljubljana (SI); Vladka Gaberc Porekar, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 85 days.

(21) Appl. No.: 12/919,625

(22) PCT Filed: Feb. 13, 2009

(86) PCT No.: PCT/EP2009/001039
§ 371 (c)(1),
(2), (4) Date: Dec. 6, 2010

(87) PCT Pub. No.: WO2009/106239
PCT Pub. Date: Sep. 3, 2009

(65) Prior Publication Data
US 2011/0092420 A1    Apr. 21, 2011

(30) Foreign Application Priority Data
Feb. 27, 2008 (EP) .................................. 08003584

(51) Int. Cl.
*C07K 17/08* (2006.01)
*A61K 38/00* (2006.01)
(52) U.S. Cl. .......................... 530/408; 514/1.1
(58) Field of Classification Search ........................ None
See application file for complete search history.

(56) References Cited

U.S. PATENT DOCUMENTS

| | | | |
|---|---|---|---|
| 5,104,852 A | 4/1992 | Kralick et al. | |
| 5,994,151 A | 11/1999 | Spallholz et al. | |
| 6,033,917 A | 3/2000 | Spallholz et al. | |
| 6,040,197 A | 3/2000 | Spallholz et al. | |
| 6,043,098 A | 3/2000 | Spallholz et al. | |
| 6,043,099 A | 3/2000 | Spallholz et al. | |
| 6,077,714 A | 6/2000 | Spallholz et al. | |
| 6,572,867 B1 | 6/2003 | Schwarz et al. | |
| 2002/0044921 A1* | 4/2002 | Lee et al. ..................... | 424/85.2 |

FOREIGN PATENT DOCUMENTS

| | | |
|---|---|---|
| EP | 1 087 791 | 9/2005 |
| WO | 2004 061094 | 7/2004 |
| WO | 2007 139997 | 12/2007 |
| WO | WO 2008/140477 A2 | 11/2008 |

OTHER PUBLICATIONS

Doherty et al., Bioconjugate Chem. 16: 1291-1298, 2005.*
Johansson et al., Biochemica et Biophysica Acta 1726: 1-13, 2005.*
Thomas, R. et al., Nanoporous Magnesium Aluminometasilicate Tablets for Precise, Controlled, and Continuous Dosing of Chemical Reagents and Catalysts: Applications in Parallel Solution-Phase Synthesis, Journal of Combinational Chemistry , vol. 9, pp. 301-305 (Mar. 2007) XP 002489145.
Sheng, S-R. et al., "Liquid-Phase Synthesis of Methyl (E)-2-Nitromethyl-2-Alkenoates Based on PEG-Supported [alpha]-Phenylselenopropionated", Synthetic Communications, vol. 37 No. 6, pp. 1011-1017 (Jan. 1, 2007)XP008093913.
Tomoda, S. et al., "Synthesis and Structures of Host Molecules Containing an Se-Se Bond. Intramolecular Hypervalent Nature of Selenium Atoms in the Crystal State", Journal of the Chemical Society, Chemical Communications, No. 3 pp. 231-233 (Jan. 1, 1990) XP 008094131.
Mazouz, A. et al., "Synthesis of Selenium-Containing Crown Ethers and Related Compounds", Phosphorus, Sulfur and Silicon and the Related Elements, vol. 61, No. 3-4, pp. 247-249 (Jan. 1, 1991) XP 008094116.
International Preliminary Report on Patentability issued Sep. 10, 2010 in Application No. PCT/EP2009/001039.
Office Action issued Mar. 11, 2011 in Europe Application No. 09 715 402.5.

* cited by examiner

*Primary Examiner* — Gyan Chandra
(74) *Attorney, Agent, or Firm* — Jun He Law Offices P.C.; Steven X. Cui

(57) ABSTRACT

The invention relates to a modifying agent comprising a water soluble polymer, wherein the water soluble polymer comprises at least one reactive selenium group, said reactive selenium group being capable of reacting with a thiol group thereby forming an —Se—S— bond. Furthermore, the invention relates to a method for producing said modifying agents and their use in the modification of pharmaceutically active agents, e.g. G-CSF. Additionally, the invention concerns conjugates comprising a water-soluble polymer and a pharmaceutically active agent, wherein the water-soluble polymer is linked via a S—Se-bond to agent and a method for their production and their use as medicaments. Finally, the invention concerns a pharmaceutical composition comprising the inventive conjugates.

4 Claims, 4 Drawing Sheets

SEQUENCE LISTING

```
<160> NUMBER OF SEQ ID NOS: 1

<210> SEQ ID NO 1
<211> LENGTH: 175
<212> TYPE: PRT
<213> ORGANISM: Escherichia coli

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
```

```
                35                  40                  45
Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

SELENIUM CONTAINING MODIFYING AGENTS AND CONJUGATES

CROSS-REFERENCE TO RELATED APPLICATIONS

Figure 1:
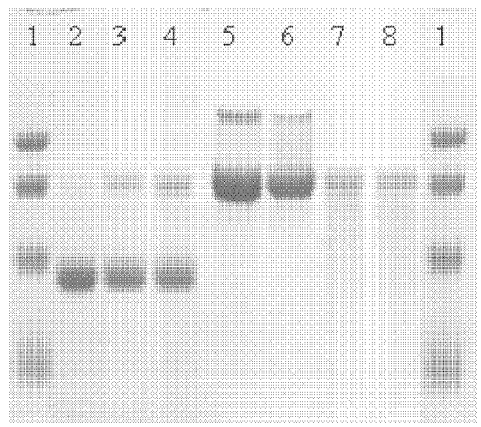

The present application is a 35 U.S.C. §371 National Stage patent application of International patent application PCT/EP2009/001039, filed on Feb. 13, 2009, which claims priority to European patent application EP 08003584.3, filed on Feb. 27, 2008.

The invention relates to modifying agents comprising a water soluble polymer, wherein the water soluble polymer comprises at least one reactive selenium group, said reactive selenium group being capable of reacting with a thiol group, preferably with a thiol group of a pharmaceutically active agent, thereby forming an —S—Se— bond. Furthermore, the invention relates to a method for producing said modifying agents and their use in the modification of pharmaceutically active agents, e.g. G-CSF. Additionally, the invention concerns conjugates comprising a water-soluble polymer and a pharmaceutically active agent, wherein the water-soluble polymer is linked via a S—Se-bond to the pharmaceutically active agent and a method for their production and their use as medicaments. Finally, the invention concerns a pharmaceutical composition comprising the inventive conjugates.

In the past few years, the number of pharmaceutically active agents like recombinant proteins and peptides has risen dramatically. But many of these proteins and peptides are not suitable for therapeutic use because of their short in-vivo half-life, immunogenicity, low proteolytic resistance or low solubility. To overcome these shortcomings different solutions were applied. One of them is chemical modification of proteins and peptides by attaching water-soluble polymers, especially polyethylene glycol. This approach, known as pegylation, has proven to be effective in improvement of the protein properties. Attachment of PEG chains to the protein increases its molecular weight and extends in-vivo half-life. The PEG chains wrapped around the protein have a shielding effect on the protein and thus proteolytic degradation and immunogenicity of the conjugate are lowered.

PEG is most commonly attached to proteins and peptides through the amino group of lysine residues and the amino group of the N-terminal amino acid. The number of lysines on the protein surface is usually high, and for that reason pegylation of lysine amino groups results in the formation of complex mixtures with positional isomers and multipegylated forms.

Cysteine residues, which are typically less frequent than lysine residues, offer a further desirable possibility for a site-specific pegylation. PEG reagents with different reactive groups can be used for a modification of a free thiol residue. In the art PEG reagents with thiol and disulfide (protected thiol) reactive groups were suggested. However, such PEG reagents form with thiol a disulfide bond, which can be easily cleaved in reducing environment. Currently two commercial PEG reagents are available for modification of proteins by forming the disulfide bond having the above-mentioned drawback. Said reagents are based on PEG-thiol and PEG-orthopyridyldisulfide agents and described in US 2005/0014903 A1. Similar, in EP 1 586 334 a process for the pegylation of Cys18 of G-CSF is suggested. However, the process leads to conjugates having a —S—S-bond, including the above-mentioned drawbacks.

Therefore, it was an object of the present invention to provide an advantageous agent for the modification of pharmaceutically active agents comprising at least one thiol group, such as polypeptides comprising at least one free cysteine group. Preferably, the modification should be reversible.

In particular, it was an object of the present invention to provide a modifying agent for the modification of pharmaceutically active agents comprising at least one thiol group, wherein the reaction time should be short. In addition, a low excess of modifying agent should be necessary. Moreover, a site-specific pegylation should be achieved.

It was a further object of the invention to provide an easy and reliable process for producing conjugates, comprising a water-soluble polymer and a pharmaceutically active agent, wherein the water-soluble polymer should be linked via a thiol group of the pharmaceutically active agent.

Generally, commercially available thiol reactive PEG reagents can be used only in alkaline conditions, where usually unwanted side reaction such as formation of disulfide connected dimers and multimers of the protein takes place. Therefore, it was a further object of the invention to provide thiol reactive PEG reagents which can be used also in acidic conditions although it was expected that reaction rate would be slower than compared to alkaline conditions. Usually, proteins that contain surface exposed cysteine-residues can spontaneously oxidize into disulfide connected dimers and multimers. This reaction is slower at acidic conditions and thus it is an advantage that the modifying reaction with the inventive modifying agent can be performed at acidic pH.

Finally, it was an object of the invention to provide a pharmaceutical composition comprising a conjugate of the present invention.

The objects of the invention could be unexpectedly solved by using a modifying agent comprising a selenium group, especially a selenium group, which reacts with thiol groups.

Therefore, subject-matter of the present invention is a modifying agent comprising a water soluble polymer, wherein the water-soluble polymer comprises at least one reactive selenium group, said reactive selenium group being capable of reacting with a thiol group (—SH), thereby forming an selenium-sulfur-bond (S—Se-bond).

The modifying agent comprises two essential features:
(1) A water soluble polymer; and
(2) a reactive selenium group.

Optionally, the modifying agent comprises additionally a (3) linking group, wherein usually the linking group links the water-soluble polymer and the reactive selenium group.

With regard to the features (1), (2) and (3) the following remarks are made.

A water-soluble polymer (1) is any polymer that is soluble in water at 25° C. Typically, a water-soluble polymer will be at least about 40% (by weight) soluble in water, more preferably at least about 55% (by weight) soluble in water, still more preferably about 75% (by weight) soluble in water, and particularly preferred about 90% (by weight) soluble in water. It is most preferred, that the water-soluble polymer or segment is about 95% (by weight) soluble in water or completely soluble in water, wherein all solubility data refers to 25° C.

The water-soluble polymers (1) can have different geometries, for example linear, branched, forked and multi-armed. Water-soluble polymers having a linear structure are preferred. The water-soluble polymers can include monofunctional, homobifunctional and heterobifunctional polymers.

The water-soluble polymer (1), e.g. a polyethylene glycol, usually has a weight average molecular weight from 300 to 100,000 daltons (Da), preferably from 1000 to 60,000 daltons, more preferably from 6000 to 40,000 daltons and particularly preferred from 10,000 to 40,000. In a preferred embodiment, the polymer has a molecular weight ranging from 20,000 to 40,000 daltons. One preferred polymer has a molecular weight of about 20,000 daltons.

Examples for suitable water-soluble polymers (1) are polyvinylpyrrolidone, polyvinylalcohol, polyols (such as polyether polyols or polyester polyols), polyalkylene oxides such as polyethylene glycol (PEG), cellulose, sucrose, hydroxyalkylstarch (HAS) and hydroxyethyl starch (HES).

In a preferred embodiment the water-soluble polymer is hydroxyalkylstarch (HAS) or particularly hydroxyethyl starch (HES). In the context of the present invention, the term "hydroxyalkylstarch" is used to indicate starch derivatives, which have been substituted by hydroxyalkylgroups. In this context, the alkyl group may be substituted. Preferably, the hydroxyalkyl contains 2-10 carbon atoms, more preferably 2-4 carbon atoms. "Hydroxyalkylstarch" therefore preferably comprises hydroxyethylstarch, hydroxypropylstarch and hydroxybutylstarch, wherein hydroxyethylstarch and hydroxypropylstarch are preferred. The hydroxyalkylgroup(s) of HAS contain at least one OH-group. The expression "hydroxyalkylstarch" also includes derivatives wherein the alkyl group is mono- or polysubstituted. In this context, it is preferred that the alkyl group is substituted with an halogen, especially flourine, or with an aryl group, provided that the HAS remains water soluble. Furthermore, the terminal hydroxy group of hydroxyalkyl may be esterified or etherified. In addition, the alkyl group of the hydroxyalkylstarch may be linear or branched. Furthermore, instead of alkyl, also linear or branched substituted or unsubstituted alkene groups may be used.

Hydroxyethylstarch (HES) is a preferred HAS in the context of the present invention. Hydroxyethylstarch (HES) is a derivative of naturally occurring amylopektine and is degraded by a-Amylase in the body. The preparation of HES-protein-conjugates is described in the state of the art (see, e.g., HES-hemoglobinconjugates in DE 26 16 086 or DE 26 46 854). HES is a substituted derivative of the carbohydrate polymer amylopektine, which is present in corn starch at a concentration of up to 95% per weight. HES exhibits advantageous biological properties and is used as a bloodvolume replacement agent and in hemodilution therapy in the clinics. Amylopektine consists of glucose moieties, wherein in the main chain a-1,4-glycosidic bonds are present and at the branching sites a-1,6-glycosidic bonds are found. The physical-chemical properties of this molecule are mainly determined by the type of glycosidic bonds. Due to the nicked a-1,4-glycosidic bond, helical structures with about six glucose-monomers per turn are produced.

In the context of the invention, hydroxyethylstarch may have a mean molecular weight (weight mean) of 1-300 kDa, wherein a mean molecular weight of 5-100 kDa is more preferred. Hydroxyethylstarch can further exhibit a molar degree of substitution of 0.1 to 0.8 and a ratio between C2:C6-substitution in the range of 2-20, with respect to the hydroxyethylgroups.

In a more preferred embodiment the water-soluble polymer is a polyalkylene oxide, especially polyethylene glycol (hereinafter referred to as PEG). "PEG" or "polyethylene glycol" as used herein comprises one of the two following structures: "—$(CH_2CH_2O)_n$—" or "—$(CH_2CH_2O)_n$—$CH_2CH_2$—,". The variable "n" ranges from 3 to 4000, preferably from 10 to 3500, more preferably from 55 to 2500, still more preferably from 80 to 1500, particularly preferred from 150 to 900. If PEG is branched, the —$(CH_2CH_2O)_n$-chain can be interrupted with one or more branching units.

The PEG residue can be e.g. monofunctional, bifunctional or polyfunctional. When PEG is monofunctional (which is preferred), the PEG residue comprises an end-capping moiety R, i.e. PEG is R—$(CH_2CH_2O)_n$—. R e.g. can be hydrogen, hydroxy or $C_1$-$C_{20}$-alkoxy. Preferably R is hydroxy, methoxy, ethoxy or benzyloxy, methoxy being particularly preferred.

Furthermore, PEG can be linear and branched. If PEG is branched, the above-mentioned linear structure is interrupted by a branching unit.

Generally, the reactive selenium group (2) is any selenium group that reacts readily or at a practical rate under conventional conditions. In the present invention the reactive selenium group (2) is capable of reacting with a thiol group (—SH), thereby forming a Se—S-bond.

In a preferred embodiment the reactive selenium group (2) comprises a diselenide group (—Se—Se—), a selenosulfite group (—$SeSO_3^-$), a selenol group (—SeH) or a selenoate group (—$Se^-$). More preferred, the reactive selenium group (2) comprises a diselenide group (—Se—Se—) or a selenosulfite group (—$SeSO_3^-$).

Optionally, the modifying agent of the present invention further comprises a linking group (3). The term "linking group" is used herein to refer to an atom or a collection of atoms optionally used to link interconnecting moieties, preferably used to link the water-soluble polymer and the reactive selenium group. The linking groups of the invention are preferably hydrolytically stable.

Usually, the linking group comprises a bridge of 1 to 10 bridging atoms, preferably 2 to 6 bridging atoms, wherein the bridging atoms optionally may comprise side chains, e.g. alkyl or alkoxy residues.

Examples for suitable linking groups are —$CH_2$—, —$CH_2$—$CH_2$—, —$CH_2$—$CH_2$—$CH_2$—, —$CH_2$—$CH_2$—$CH_2CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2CH_2$—$CH_2$—O—, —O—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —CO—NH—$CH_2$—$CH_2$—$CH_2$—$CH_2$—, —$CH_2$—CO—NH—$CH_2$—$CH_2$—$CH_2$—, —CO—NH—$CH_2$—, —CO—NH—$CH_2$—$CH_2$—, —$CH_2$—CO—NH—$CH_2$—, —$CH_2$—$CH_2$—CO—NH—, —CO—NH—$CH_2$—$CH_2$—$CH_2$—, —$CH_2$—CO—NH—$CH_2$—$CH_2$—, —$CH_2$—$CH_2$—CO—NH—$CH_2$—, —$CH_2$—$CH_2$—$CH_2$—CO—NH—, —$CH_2$—CO—NH—$CH_2$—$CH_2$—, —$CH_2$—$CH_2$—CO—NH—$CH_2$—, —$CH_2$—$CH_2$—$CH_2$—CO—NH—, —$CH_2$—$CH_2$—$CH_2$—CO—NH—, —CO—O—$CH_2$—, —$CH_2$—CO—O—$CH_2$—, —$CH_2$—$CH_2$—CO—O—$CH_2$—, —CO—O—$CH_2$—$CH_2$—, —O—CO—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —CO—$CH_2$—, —CO—$CH_2$—$CH_2$—, —$CH_2$—CO—$CH_2$—, —$CH_2$—$CH_2$—CO—$CH_2$—, —$CH_2$—$CH_2$—CO—$CH_2$—$CH_2$—, —$CH_2$—$CH_2$—CO—, —NH—CO—$CH_2$—, —$CH_2$—NH—CO—$CH_2$—, —$CH_2$—$CH_2$—NH—CO—$CH_2$—, —NH—CO—$CH_2$—$CH_2$—, —$CH_2$—NH—CO—$CH_2$—$CH_2$—, —$CH_2$—$CH_2$—NH—CO—$CH_2$—$CH_2$—, —NH—CO—$CH_2$—$CH_2$—, —CO—NH—$CH_2$—, —CO—NH—$CH_2$—$CH_2$—, —O—CO—NH—$CH_2$—, and combinations of two or more of any of the foregoing.

Preferably, the linking group is —CO—NH—CHR—$CH_2$—, wherein R is hydrogen, carboxyl or $C_1$-$C_6$ alkyl, in particular R is hydrogen or carboxyl.

Subject-matter of a preferred embodiment of the present invention is a modifying agent having a structure as described in formula I or II,

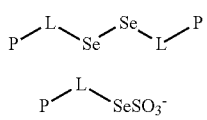

(I)

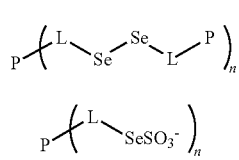

(II)

wherein in above formulae P is a water-soluble polymer and L is a linking group. Preferably, P and L are chosen from the water-soluble polymers and linking groups, respectively, as described above. Especially, P is a PEG residue and L is —CO—NH—CHR—CH$_2$—, wherein R is hydrogen, carboxyl or C$_1$-C$_6$ alkyl, in particular R is hydrogen or carboxyl.

As described above, the water-soluble polymer could be bifunctional or polyfunctional. Hence, subject-matter of the present invention is also a modifying agent having a structure as described in formula Ia or IIa,

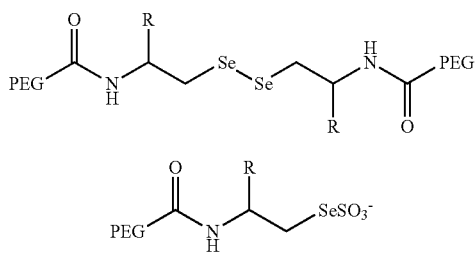

(Ia)

(IIa)

wherein in above formulae P is a water-soluble polymer, L is a linking group and n is a number from 2 to 10. Preferably, P and L is chosen from the water-soluble polymers and linking groups, respectively, as described above. Furthermore, n preferably is 2, 3 or 4, in particular 2. Especially, P is a PEG residue and L is —CO—NH—CHR—CH$_2$—, wherein R is hydrogen, carboxyl or C$_1$-C$_6$ alkyl, in particular R is hydrogen or carboxyl.

Subject-matter of a particularly preferred embodiment of the present invention is a modifying agent having a structure as described in formula III or IV, (III)

(IV)

wherein in above formulae PEG is polyethylene glycol and R is hydrogen, carboxyl or C$_1$-C$_6$ alkyl. The above mentioned preferred embodiments of PEG (e.g. molecular weight, end-capping groups) also apply for PEG in the formulae III and IV.

A further subject of the present invention is also a process for producing the above-mentioned inventive modifying agents.

Hence, the present invention comprises a process for producing the inventive modifying agent, comprising the steps
(i) providing a compound of formula V

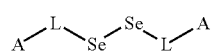

(V)

wherein A is an functional group and L is a linking group,
(ii) reacting the compound of formula V with an activated water soluble polymer and
(iii) optionally subjecting the product of step (ii) to a sulfitolysis reaction.

The product resulting in step (ii) corresponds to compounds according to formulae I, Ia, and III. The product resulting in the additional reaction step (iii) corresponds to compounds according to formulae II, IIa, and IV.

In step (i) of the inventive process a compound according to formula V is provided. The compound according to formula V comprises a diselenide bond, two linking groups L and two functional groups A.

Regarding to the linking group L it is referred to the above-mentioned preferred embodiments. Preferably, the linking group is —CHR—CH$_2$—, wherein R is hydrogen, carboxyl or C$_1$-C$_6$ alkyl, particularly hydrogen or carboxyl.

The functional group A is capable of reacting with the activated water-soluble polymer and preferably is capable of forming a stable linkage. The functional group A preferably is selected from amino, hydroxyl and carboxyl. Most preferably, the functional group A is a primary amino group, i.e. A is —NH$_2$.

The compound according to formula V is reacted in step (ii) with an "activated water-soluble polymer". The term activated water-soluble polymer comprises any water-soluble polymer as defined above, that comprises one or more groups, which can react with the above defined functional group A of formula V. Examples for reactive groups are N-hydroxy-succinimide esters, dichlorotriazine, tresylate, succinimidyl carbonate, benzotriazole carbonate, p-nitro-phenyl carbonate, trichlorophenyl carbonate, carbonilimidazole, isocyanate, isothiocyanate and aldehyde reactive group.

Preferably, in step (ii) an activated PEG is used, i.e. PEG reagents with N-hydroxysuccinimide esters, dichlorotriazine, tresylate, succinimidyl carbonate, benzotriazole carbonate, p-nitrophenyl carbonate, trichlorophenyl carbonate, carbonilimidazole and aldehyde reactive group. In particular, a polyethylene glycol being activated with a N-hydroxysuccinimide ester residue (hereinafter referred to as PEG-NHS) is used.

With regard to preferred embodiments the following is noted: If the functional group "A" of formula V is amino group than "activated water-soluble polymer" (preferably the activated PEG) comprises one or more amino-reactive groups. If "A" is carboxyl group, "activated water-soluble polymer" comprises one or more hydrazide groups. If "A" is hydroxyl group, "activated water-soluble polymer" comprises one or more isocyanate groups. Alternatively, the opposite approach is also possible. That is, that the activated water-soluble polymer (preferably the activated PEG) bears amino, hydroxyl or carboxyl group, and that "A" is a suitable functional group as stated above for the activated water-soluble polymer.

Hence, in a preferred embodiment of the inventive process in step (i) a compound according to formula VI is provided

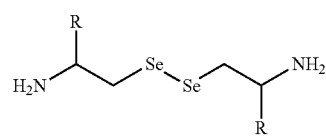

(VI)

wherein in above formula R is hydrogen or carboxyl,
and in step (ii) the compound according to formula VI is reacted with PEG-NHS. The compound according to formula VI is a more specific embodiment of the compound according to formula V.

It is particularly preferred that selenocystine (R=COOH) or selenocystamine (R=H) are used as compound according to formula VI.

The coupling reaction (ii) can be performed in aqueous or non-aqueous solution. The pH may range from 6 to 10, preferably from 7.5 to 8.5. The reaction can be carried out e.g. from 10 to 50° C., preferably from 20 to 30° C. The reaction time may vary, e.g. from 1 hour to 20 hours.

While selenocystamine is readily dissolved in aqueous solutions, the slow dissolution rate of selenocystine preferably can be increased through an alkaline solution, e.g. 1M KOH. However, for reaction with PEG-NHS the pH of the solution has to be reduced. When the coupling reaction is finished, residual selenocystine can be removed from the mixture by ultrafiltration or by organic-phase extraction. The latter provides the isolation of PEG mixture in the solid form. Generally, unreacted PEG-NHS does not need to be removed, because it hydrolyses with time into non-reactive form. The amount of disubstituted selenocystine or selenocystamine can be qualitatively estimated by SDS-polyacrylamide gel electrophoresis (SDS-PAGE) or by reversed phase chromatography (RP-HPLC). Both methods are applicable because the reaction product of step (ii) (hereinafter referred to also as $(PEG-Se)_2$) is twice as large as the starting material (PEG-NHS).

The preferred embodiment comprising reactions steps (i) and (ii) is illustrated by the reaction scheme shown below:

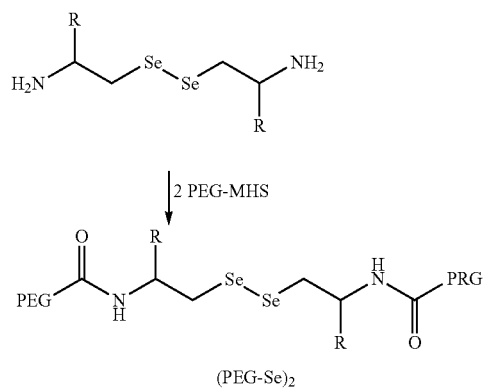

wherein R preferably is H or COOH.

In the additional reaction step (iii) the modifying agent comprising a diselenide group can be reacted to give a modifying agent comprising a selenosulfite group.

The reaction (iii) is a so-called sulfitolysis. For carrying out the reaction step (iii), sulfitolysis reagents can be used. A suitable sulfitolysis reagent may be prepared by mixing $Na_2SO_3$ and $Na_2S_4O_6$. The reaction can be carried out in an aqueous solution. The solution preferably is buffered. The pH may range from 7 to 10, preferably from 8 to 9. The reaction can be carried out e.g. from 10 to 50° C., preferably from 20 to 30° C. The reaction time may vary, e.g. from 1 hour to 20 hours.

The formation of monomeric form ($=PEG-SeSO_3^-$) can be monitored, e.g. by SDS-PAGE. When the reaction is finished low molecular mass reagents could be removed, e.g. by ultrafiltration.

A preferred embodiment comprising reactions steps (i) to (iii) is illustrated by the reaction scheme shown below

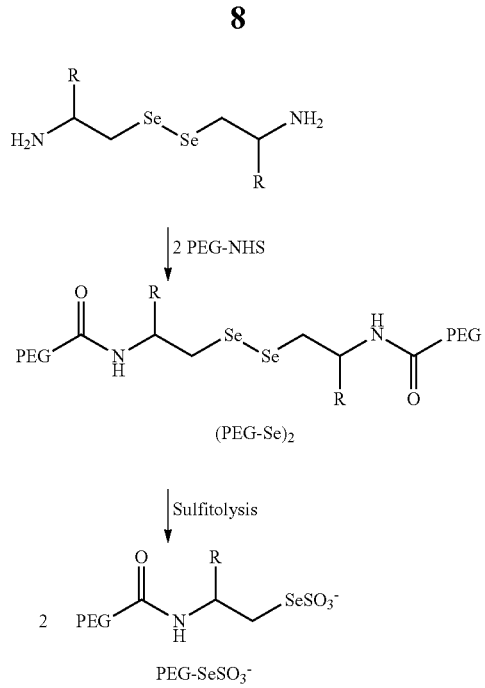

wherein R preferably is H or COOH.

Both forms of the modifying agents (dimeric, i.e. reaction product of step (ii) as well as monomeric, i.e. reaction product of step (iii)) may contain impurities related with un-reacted activated water-soluble polymer, e.g. PEG-NHS reagent. These impurities do not need to be removed, since they do not interfere in the conjunction reaction, e.g. in the pegylation reaction of thiol containing active agents, e.g. of the thiol containing proteins.

Optionally, unreacted activated water-soluble polymers can be removed by using different chromatographic techniques, e.g. selected from ion exchange chromatography, size exclusion or reversed phase chromatography. In the case of dimeric Se-PEG reagents prepared from selenocystine and monomeric Se-PEG reagents, ion exchange chromatography could be used, due to the presence of negative charge. The dimeric Se-PEG reagent prepared from selenocystamine can be efficiently purified by size exclusion or reversed phase chromatography.

The modifying agents of the present invention can be used for attaching a water-soluble polymer to a pharmaceutically active agent comprising a thiol group, preferably to a cysteine residue of a polypeptide. When the water-soluble polymer is PEG, the modifying agent can be used for the pegylation of a pharmaceutically active agent comprising a thiol group, in particular for the pegylation of a cysteine residue of a polypeptide. Preferably, the modifying agent of the present invention is used for the pegylation of G-CSF, wherein in particular Cys18 of G-CSF is pegylated, more particularly monopegylated.

Consequently, subject-matter of the present invention further is a conjugate comprising a water-soluble polymer and a pharmaceutically active agent comprising a thiol group, wherein the water-soluble polymer is linked via a S—Se— bond to the pharmaceutically active agent.

Hence, a further subject of the present invention is a process for the preparation of a conjugate of the present invention, comprising the steps
(i) providing a pharmaceutically active agent having at least one free thiol group and (ii) reacting said pharmaceutically active agent with a modifying agent according to the present invention.

That means, pharmaceutically active agent comprising a thiol group like proteins, peptides or amino acids with free thiol group can react with the inventive modifying agents. By this reaction a covalent linkage is formed via selenylsulfide bond, as illustrated in the schemes below.

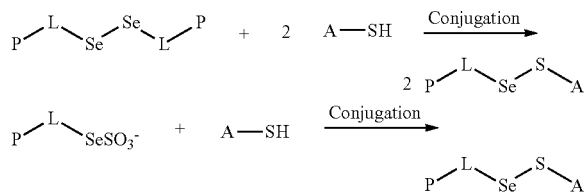

A is a pharmaceutically active agent, preferably a polypeptide, having a free cysteine residue.

Similar reactions may occur when the water-soluble polymer is bi- or polyfunctional, see reaction schemes below.

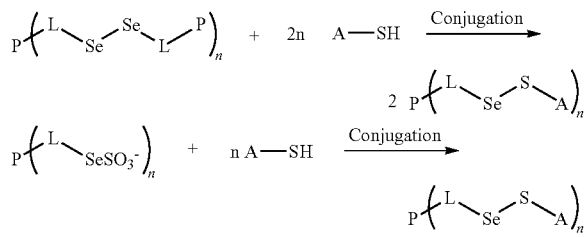

A is a pharmaceutically active agent, preferably a polypeptide, having a free cysteine residue. n is a natural number, preferably from 2 to 10, more preferably 2, 3 or 4.

Generally, the term "pharmaceutically active agent" refers to any agent, drug, compound, composition or mixture which provides some pharmacologic, preferably some beneficial, effect that can be demonstrated in-vivo or in vitro.

General examples of pharmaceutically active agents are peptides, polypeptides, proteins, antibodies and antibody derivatives, polysaccharides, steroids, nucleotides, oligonucleotides, polynucleotides, fats, electrolytes, and mixtures thereof.

Specific examples of suitable pharmaceutically active agents are aspariginase, amdoxovir (DAPD), becaplermin, bisphosphonates, calcitonins, cyanovirin, denileukin, diftitox, erythropoietin (EPO), erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (G-CSF), thrombopoietin (TPO), alpha-1 proteinase inhibitor, elcatonin, granulocyte macrophage colony stimulating factor (GM-CSF), fibrinogen, follicle stimulating hormone (FSH), human growth hormone (hGH), growth hormone releasing hormone (GHRH), GRO-beta, GRO-beta antibody, acidic fibroblast growth factor, basic fibroblast growth factor, CD-40 ligand, heparin, human serum albumin, interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor, insulin, low molecular weight heparin (LMWH), pro-insulin, influenza vaccine, insulin-like growth factor (IGF), insulintropin, macrophage colony stimulating factor (M-CSF), monoclonal antibodies, plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T-cell receptors, CD molecules/antigens, tumor necrosis factor (TNF), monocyte chemoattractant protein-1, endothelial growth factors, parathyroid hormone (PTH), or mixtures thereof. It is essential, that the above mentionded active agents comprise a free thiol group or are modified in a way that they comprise a free thiol group. "Free thiol group" means a thiol group (—SH) which is not linked to another thiol group via a disulfide bond.

Examples for antibodies are known, e.g. antibodies directed against HER2 (e.g. trastuzumab), VEGF (e.g. bevacizumab), EGF (e.g. cetuximab), CD20 (e.g. rituximab), TNF (e.g. infliximab, adalimumab). Examples for derivatives of antibodies are also known and comprise e.g. immune globulin Fc fusion proteins (e.g. etanercept) or Fab fragments (e.g. ranibizumab).

Preferably, the pharmaceutically active agent is a polypeptide, comprising at least one free thiol group, preferably belonging to a cysteine residue of the polypeptide. That means, usually the thiol groups can belong to naturally present unpaired cysteine residues but they can also be either chemically or genetically introduced into the protein structure. Alternatively, a free thiol group can also be achieved by reduction of disulfide bonds of the protein (if this disulfide bond is not necessary for the desired biological activity of protein).

Examples of preferred polypeptides are EPO, IFN-[alpha], IFN-[beta], IFN-[gamma], consensus IFN, Factor VII, Factor VIII, Factor IX, G-CSF, GM-CSF, hGH, insulin, FSH, PTH or mixtures thereof. Particularly preferred is C—CSF. Alternatively, EPO is particularly preferred.

Generally, the present invention preferably employs purified and isolated polypeptides having part or all of the primary structural conformation (i.e., continuous sequence of amino acid residues) and one or more of the biological properties (e.g., immunological properties and in vitro biological activity) and physical properties (e.g., molecular weight). These polypeptides are also characterized by being the product of chemical synthetic procedures or of procaryotic or eucaryotic host expression (e.g., by bacterial, yeast, higher plant, insect and mammalian cells in culture) of exogenous DNA sequences obtained by genomic or cDNA cloning or by gene synthesis. The products of typical yeast (e.g., *Saccaromyces cerevisiae*) or procaryote [e.g., *Escherichia coli (E. coli)*] host cells are free of association with any mammalian proteins. The products of microbial expression in vertebrate (e.g., non-human mammalian and avian) cells are free of association with any human proteins. Depending upon the host employed, polypeptides used in the invention may be glycosylated with mammalian or other eucaryotic carbohydrates or may be non-glycosylated. Polypeptides of the invention may also include an initial methionine amino acid residue (at position −1).

Especially recombinant human granulocyte-colony stimulating factor (G-CSF) produced in *E. coli* is used. The amino acid sequence of the preferred G-CSF is shown in SEQ ID No: 1. The amino acid sequence shown in SEQ ID No: 1 is preferably not glycosylated and is commercially available as Filgrastim. Alternatively, especially recombinant human granulocyte-colony stimulating factor (G-CSF) produced by eucaryotic host expression is used. The amino acid sequence of this preferred embodiment is the same as shown in SEQ ID No: 1, provided that Met1 is absent. Additionally, the polypeptide of this preferred embodiment is glycosylated and is commercially available as Lenograstim.

In a further preferred embodiment also erythropoietin (EPO) and its derivatives may be used. EPO as such is well known in the art. Erythropoietin is an acid glycoprotein hormone of approximately 34 kDa. Human erythropoietin is a 166 amino acid polypeptide that exists naturally as a monomer (Lin et al., 1985, PNAS 82, 7580-7584, EP 148 605 B2, EP 411 678 B2).

The EPO used in the context of the invention can be of any human or another mammalian source and can be obtained by purification from naturally occurring sources like human kidney, embryonic human liver or animal, preferably monkey kidney. Preferably, the EPO is recombinantly produced. This includes the production in eukaryotic or prokaryotic cells, preferably mammalian, insect, yeast, plant, bacterial cells or in any other cell type which is convenient for the recombinant production of EPO. Furthermore, the EPO may be expressed in transgenic animals (e.g. in body fluids like milk, blood, etc.), in eggs of transgenic birds, especially poultry, preferred chicken, or in trans-genic plants or algae.

The EPO may comprise one or more carbohydrate side chains (preferably 1-4, preferably 4) attached to the EPO via N- and/or O-linked glycosylation, i.e. the EPO is glycosylated. Usually, when EPO is produced in eukaryotic cells, the polypeptide is posttranslationally glycosylated. Consequently, the carbohydrate side chains may have been attached to the EPO during biosynthesis in mammalian, especially human, insect, plant, or yeast cells.

The recombinant production of a polypeptide is known in the art. In general, this includes the transfection of host cells with an appropriate expression vector, the cultivation of the host cells under conditions which enable the production of the polypeptide and the purification of the polypeptide from the host cells.

Particularly, the EPO may have the amino acid sequence of human EPO (see EP 148 605 B2). Furthermore, the expression "erythropoietin" or "EPO" encompasses also an EPO variant wherein one or more amino acids (e.g. 1 to 25, preferably 1 to 10, more preferred 1 to 5, most preferred 1 or 2) have been exchanged by another amino acid as compared to the sequence of human EPO and wherein the EPO exhibits erythropoietic activity (see EP 640 619 B1).

The measurement of erythropoietic activity is described in the art (for measurement of activity in vitro see e.g. Fibi et al., 1991, Blood, 77, 1203 ff; for measurement of EPO activity in vivo see e.g. Fibi, Hermentin, Pauly, Lauffer, Zettlmeissl., 1995, N- and O-glycosylation muteins of recombinant human erythropoietin secreted from BHK-21 cells, Blood, 85(5), 1229-36; (EPO and modified EPO forms were injected into female NMRI mice (equal amounts of protein 50 ng/mouse) at day 1, 2 and 3 blood samples were taken at day 4 and reticulocytes were determined)).

Generally, the above-mentioned examples of polypeptides also can encompass analogues, agonists, antagonists, inhibitors, isomers, and pharmaceutically acceptable salt forms thereof. Furthermore, the above mentioned polypeptides encompass synthetic, recombinant, native, glycosylated, and non-glycosylated forms, as well as biologically active fragments thereof, provided at least one free thiol group is present.

The meaning of the term "biologically active", particularly "biologically active fragment", is understood by the person skilled in the art. Particularly, a fragment or derivative is considered to be biologically active, if it retains the quality of biological activity of the parent molecule, even if the activity as such is increased or decreased. More particularly, biologically active means that the fragment or derivative should be therapeutically active if administered in a suitable dose.

Consequently, subject-matter of a preferred embodiment of the present invention is a conjugate, having a structure in accordance with formula VII

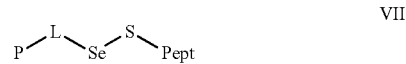

VII wherein in above formula P is a water soluble polymer, L is a linking group, Se is a selenium atom, Pept is a polypeptide and S is a sulfur atom belonging to a cysteine residue of the polypeptide. With regard to P, L and Pept it is referred to the explanations given above for preferred embodiments.

In a particular preferred embodiment the present invention relates to a conjugate, having a structure in accordance with formula VIII

Figure 8:
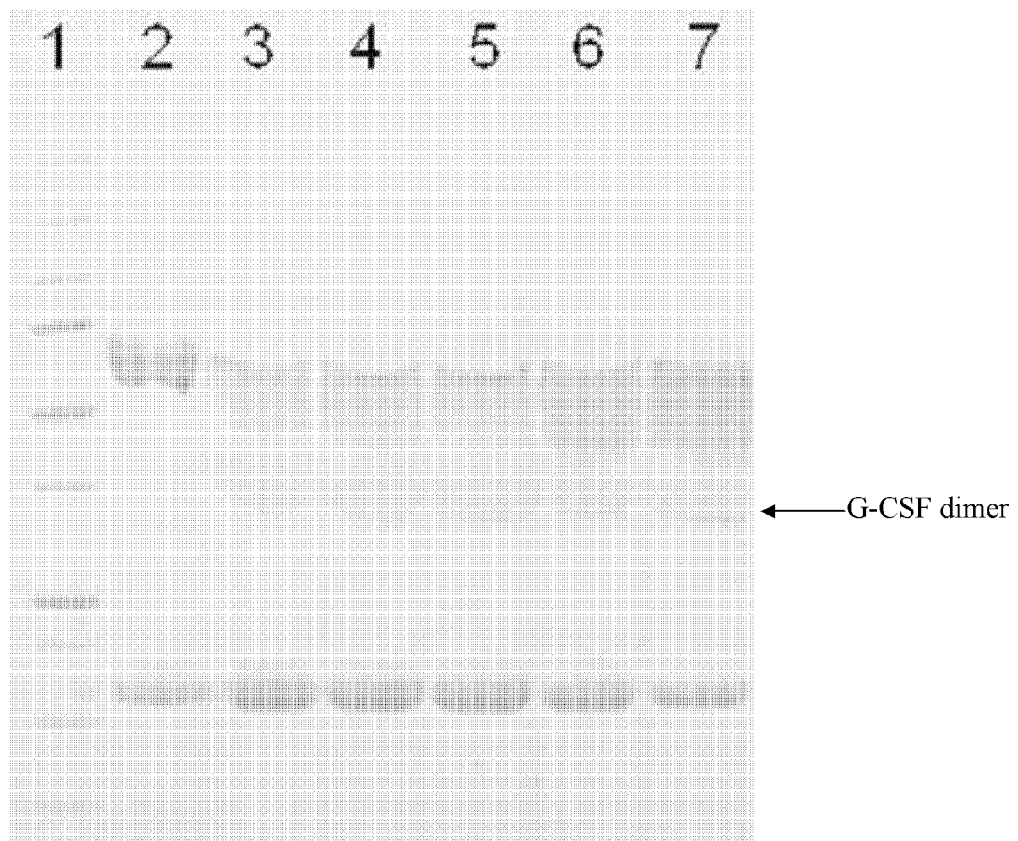

VIII wherein in above formula PEG is polyethylene glycol, L is a linking group, preferably is a —CO—NH—CHR—CH$_2$— residue, wherein R is hydrogen, carboxyl or C$_1$-C$_6$ alkyl, Se is a selenium atom, G-CSF is granulocyte colony-stimulating factor and S is a sulfur atom belonging to a cysteine residue of the granulocyte colony-stimulating factor. In formula VIII "G-CSF" preferably is a recombinant human granulocyte-colony stimulating factor (G-CSF) produced in E. coli. The amino acid sequence of the preferred G-CSF is shown in FIG. 8. Alternatively, G-CSF known as Lenograstim can be used.

It is particularly preferred that in formula VIII "S" is a sulfur atom of the Cys18 residue of G-CSF. Hence, G-CSF being monopegylated at Cys18 is particularly preferred.

The inventive conjugates can be used as medicaments. Therefore, a further subject of the present invention is inventive conjugate for use as a medicament.

In a preferred embodiment the inventive conjugate is used for the treatment of neutropenia. Especially, the treatment is in patients with non-myeloid malignancies receiving myelosuppressive anti-cancer drugs.

As discussed above, the present invention also concerns a process for the preparation of a conjugate of the present invention, comprising the steps
(i) providing a pharmaceutically active agent having at least one free thiol group and
(ii) reacting said pharmaceutically active agent with a modifying agent according to the present invention (conjugation reaction).

The conjugation reaction can be carried out in an aqueous solution. The solution preferably is buffered. The pH may range from 3 to 10, preferably from 6 to 9. The reaction can be carried out e.g. from 2 to 50° C., preferably from 20 to 30° C. Generally, the conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture e.g. by SDS-PAGE or MALDI-TOF mass. The reaction time may vary, e.g. from 1 hour to 50 hours, preferably from 10 to 25 hours.

In the process of the present invention all above made comments about preferred embodiments of the water-soluble polymer and the pharmaceutically active agent apply. Preferably, the water-soluble polymer is PEG and the active agent is G-CSF.

For pegylation of a free thiol group said thiol group preferably has to be sufficiently exposed to allow reaction with the modifying agent of the present invention. In G-CSF the Cys18 residue usually is only partially exposed to the solvent and not sufficiently accessible by the modifying agent, therefore, G-CSF preferably is reversibly denatured, (preferably under mild conditions) prior to pegylation reaction. This can be achieved by addition of various compounds, such as of urea, GdHCl, DMSO, SDS, NLS, Tweens. After the pegylation reaction preferably a renaturation step is carried out. The renaturation can be induced by buffer exchange and/or dilution.

The conjugation reaction is usually carried out in an molar excess of modifying agent. In a preferred embodiment the molar ratio of reactive selenium atoms to reactive thiol groups is from 0.9:1 to 10:1, more preferably 1.0 to 5:1, more preferably from 1.1:1 to 3:1.

The resulting conjugated product is preferably purified in order to separate out e.g. excess reagents, unconjugated reactants, undesired multi-conjugated species, and/or free or unreacted polymer. The resulting conjugates can then be further characterized using analytical methods such as MALDI, capillary electrophoresis, gel electrophoresis, and/or chromatography.

Finally, a further subject of the present invention is a pharmaceutical composition comprising
(a) a conjugate according to the present invention
(b) one or more pharmaceutically acceptable excipients.

For the conjugate (a) all the above-made comments about preferred embodiments apply.

Generally, "pharmaceutically acceptable excipient" means an excipient that can be included in the compositions of the invention and that causes no significant adverse toxicological effects to a patient.

Examples for suitable excipients are carbohydrates, antimicrobial agents, surfactants, buffers, acids, bases, antioxidants, inorganic salts, and mixtures thereof.

Examples for suitable carbohydrate excipients are monosaccharides, such as fructose, maltose, galactose, glucose, D-mannose, sorbose, disaccharides, such as lactose, sucrose, trehalose; polysaccharides, such as starches; and alditols, such as mannitol, sorbitol. Examples for an inorganic salt or buffer are citric acid, sodium chloride, potassium chloride, sodium sulfate, potassium nitrate, sodium phosphate monobasic, sodium phosphate dibasic, and combinations thereof. Examples for suitable surfactants are polysorbates, such as "Tween 20" and "Tween 80," sorbitan esters; lipids, such as phospholipids such as lecithin, fatty acids and fatty acid esters; steroids, such as cholesterol; and chelating agents, such as EDTA.

The pharmaceutical composition of the present invention comprises all types of formulations, wherein those that are suited for injection are preferred. The amount of the conjugate in the composition will vary, but will preferably be a therapeutically effective dose when the composition is stored in a unit dosage form (e.g., a vial).

The pharmaceutical preparations of the present invention are preferably administered via injection and are therefore generally liquid solutions or suspensions.

The invention should be illustrated by the following examples.

EXAMPLES

A) Methods Used in the Present Invention

SDS-PAGE (Sodium Dodecyl Sulfate Polyacrylamide Gel Electrophoresis)

SDS-PAGE was used for monitoring formation of novel Se-PEG reagents as well as for estimation of the coupling reactions between protein and Se-PEG reagents. SDS-PAGE was performed using commercially available 4%-12% Bis-Tris gels (Invitrogen). Two types of detection were used: Iodine staining for visualization of PEG and Simply Blue (Invitrogen) staining for visualization of protein.

Cation Exchange Chromatography (CEC)

CEC was used for isolating G-CSF pegylated at Cys 18 residue from the pegylation mixture. An 8 ml column (Tricorn 10/100) with SP-5PW TSK-Gel (TO—SOHAAS) was used for the separation. The binding buffer was 25 mM $CH_3COOH$/NaOH pH 3.8. Pegylated and nonpegylated forms of G-CSF were separated using a shallow linear gradient from 0 to 100% of elution buffer (75 mM $CH_3COOH$/NaOH pH 8.0) in 35 column volumes. The separation was performed at flow rate 2.0 ml/min. The CEC fractions were pooled according to the SDS-PAGE analysis performed under nonreducing conditions (Simply Blue staining and Iodine staining).

Reversed-Phase High-Performance Liquid Chromatography (RP-HPLC)

RP-HPLC was used for the analyses of the Se-PEG reagents. It was performed on Waters Bondapak™ Phenyl column (3.9×150 mm, particle size: 10 µm) by using Corona plus and Knauer UV detector. The binding eluent was 40% $CH_3CN/H_2O$. The PEG moieties were separated using linear gradient from 40-50% of $CH_3CN/H_2O$. The flow rate was 1 ml/min. Sample was prepared by dissolving the solid PEG mixture in 40% $CH_3CN/H_2O$ and injected with an injection volume of 10 l.

B) Description of the Figures

FIG. 1: The SDS-PAGE analysis of Se-PEG reagents (Iodine staining, non-reducing conditions).
Lane 1: PEG MW standard (5 kDa, 12 kDa, 20 kDa, 30 kDa)
Lane 2: Starting 10 kDa mPEG-NHS reagent
Lane 3: Reaction mixture of (PEG-Se)$_2$ reagent prepared from selenocystine and 10 kDa PEG-NHS.
Lane 4: Reaction mixture of (PEG-Se)$_2$ reagent prepared from selenocystamine and 10 kDa PEG-NHS.
Lane 5: Reaction mixture of (PEG-Se)$_2$ reagent prepared from selenocystamine and 20 kDa PEG-NHS.
Lane 6: Reaction mixture of (PEG-Se)$_2$ reagent prepared from selenocystine and 20 kDa PEG-NHS
Lane 7: Reaction mixture of PEG-SeSO$_3$ reagent prepared from selenocystamine and 20 kDa PEG-NHS.
Lane 8: Reaction mixture of PEG-SeSO$_3$ reagent prepared from selenocystine and 20 kDa PEG-NHS.

Lane 2, 3, 4, 5 and 6: The spot with higher molecular weight corresponds to (Se-PEG)$_2$ reagent and a spot with lower molecular weight corresponds to starting PEG-NHS reagent. Lane 7 and 8: The formation of PEG-SeSO$_3$ is confirmed by disappearance of high molecular weight spot that corresponds to (PEG-Se)$_2$.

Figure 2:
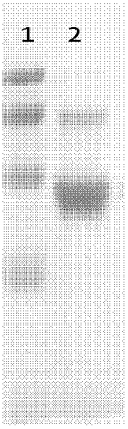

FIG. 2: The SDS-PAGE analysis of (PEG-Se)$_2$ reagent prepared in dry DMF (Iodine staining, non-reducing conditions).
Lane 1: PEG MW standard (5 kDa, 12 kDa, 20 kDa, 30 kDa)
Lane 2: Reaction mixture of (Se-PEG)$_2$ reagent prepared from selenocystine and 10 kDa PEG-NHS.

Figure 3:
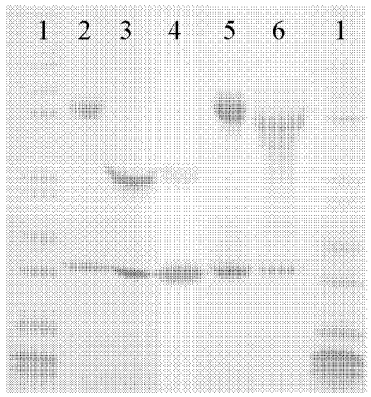

FIG. 3: The SDS-PAGE analysis of pegylation mixtures of G-CSF and different Se-PEG reagents (Simply blue staining, non-reducing conditions).
Lane 1: Protein MW standard (2.5 kDa, 3.5 kDa, 6 kDa, 14.4 kDa, 21.5 kDa, 31.0 kDa, 36.5 kDa, 55.4 kDa, 66.3 kDa, 97.4 kDa, 116.3 kDa, 200 kDa)
Lane 2: G-CSF+Neulasta
Lane 3: Pegylation mixture of G-CSF and (PEG-Se)$_2$ reagent prepared from selenocystamine and 10 kDa PEG-NHS.
Lane 4: Pegylation mixture of G-CSF and (PEG-Se)$_2$ reagent prepared from selenocystine and 10 kDa PEG-NHS.
Lane 5: Pegylation mixture of G-CSF and (PEG-Se)$_2$ reagent prepared from selenocystine and 20 kDa PEG-NHS.
Lane 6: Pegylation mixture of G-CSF and PEG-SeSO$_3$ reagent prepared from selenocystamine and 20 kDa PEG-NHS.
Lane 3 and 4: The spot with higher molecular weight corresponds to G-CSF conjugated with 10 kDa Se-PEG reagent and the spot with lower molecular weight corresponds to native G-CSF.
Lane 5 and 6: The spot with higher molecular weight corresponds to G-CSF conjugated with 20 kDa Se-PEG reagent and the spot with lower molecular weight corresponds to native G-CSF.

Figure 4:
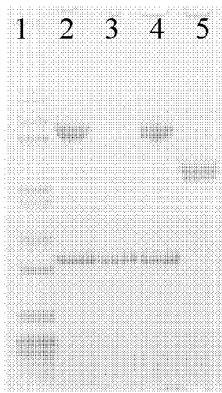

FIG. 4: The SDS-PAGE analysis of purified G-CSF conjugate, prepared with (PEG-Se)$_2$ reagent (Simply blue staining, reducing and non-reducing conditions).
Lane 1: Protein MW standard (2.5 kDa, 3.5 kDa, 6 kDa, 14.4 kDa, 21.5 kDa, 31.0 kDa, 36.5 Da, 55.4 kDa, 66.3 kDa, 97.4 kDa, 116.3 kDa, 200 kDa)
Lane 2: G-CSF+Neulasta; reducing conditions
Lane 3: G-CSF conjugate with 10 kDa PEG attached to Cys 18 (prepared with (PEG-Se)$_2$ from selenocystamine and 10 kDa PEG-NHS); reducing conditions
Lane 4: G-CSF+Neulasta; non-reducing conditions
Lane 5: G-CSF conjugate with 10 kDa PEG attached to Cys 18 (prepared with (PEG-Se)$_2$ from selenocystamine and 10 kDa PEG-NHS); non-reducing conditions At nonreducing conditions single high molecular weight band is seen and it corresponds to pegylated G-CSF. Under reducing conditions PEG is cleaved from the protein and single band is seen with molecular weight corresponding to native G-CSF.

Figure 5:
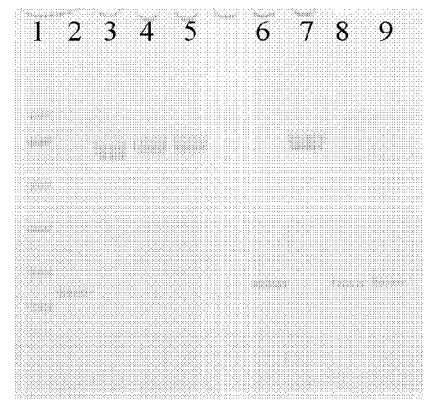

FIG. 5: The SDS-PAGE analysis of purified G-CSF conjugates, prepared with (PEG-Se)$_2$ or PEG-SeSO$_3$ reagent (Simply blue staining, reducing and non-reducing conditions).
Lane 1: Protein MW standard (15 kDa, 21 kDa, 31 kDa, 50 kDa, 66 kDa, 100 kDa)
Lane 2: G-CSF; non-reducing conditions
Lane 3: Neulasta; non-reducing conditions
Lane 4: G-CSF conjugate with 20 kDa PEG attached to Cys 18 (prepared with (PEG-Se)$_2$ from selenocystamine and 20 kDa PEG-NHS); non-reducing conditions
Lane 5: G-CSF conjugate with 20 kDa PEG attached to Cys 18 (prepared with PEG-SeSO$_3$ from selenocystamine and 20 kDa PEG-NHS); non-reducing conditions
Lane 6: G-CSF; reducing conditions
Lane 7: Neulasta; reducing conditions
Lane 8: G-CSF conjugate with 20 kDa PEG attached to Cys 18 (prepared with (PEG-Se)$_2$ from selenocystamine and 20 kDa PEG-NHS); reducing conditions
Lane 9: G-CSF conjugate with 20 kDa PEG attached to Cys 18 (prepared with (PEG-Se)$_2$ from selenocystamine and 20 kDa PEG-NHS); reducing conditions At non-reducing conditions single high molecular weight band is seen and it corresponds to pegylated G-CSF. Under reducing conditions PEG is cleaved from the protein and single band is seen with molecular weight corresponding to native G-CSF.

Figure 6:
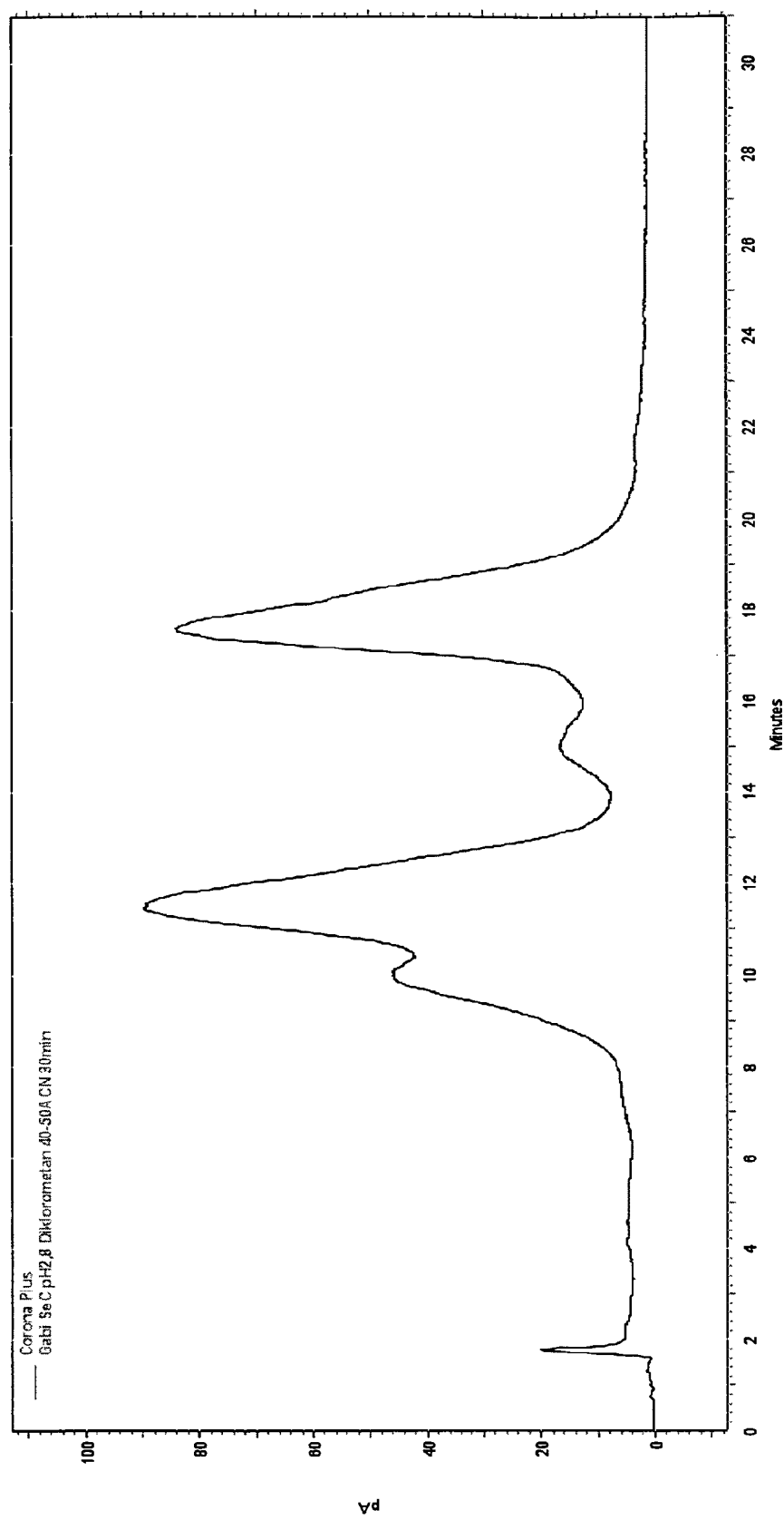

FIG. 6: RP-HPLC chromatogram (Corona detector) of the reaction mixture of (PEG-Se)$_2$ reagent prepared from selenocystine and 20 kDa PEG-NHS.

Figure 7:
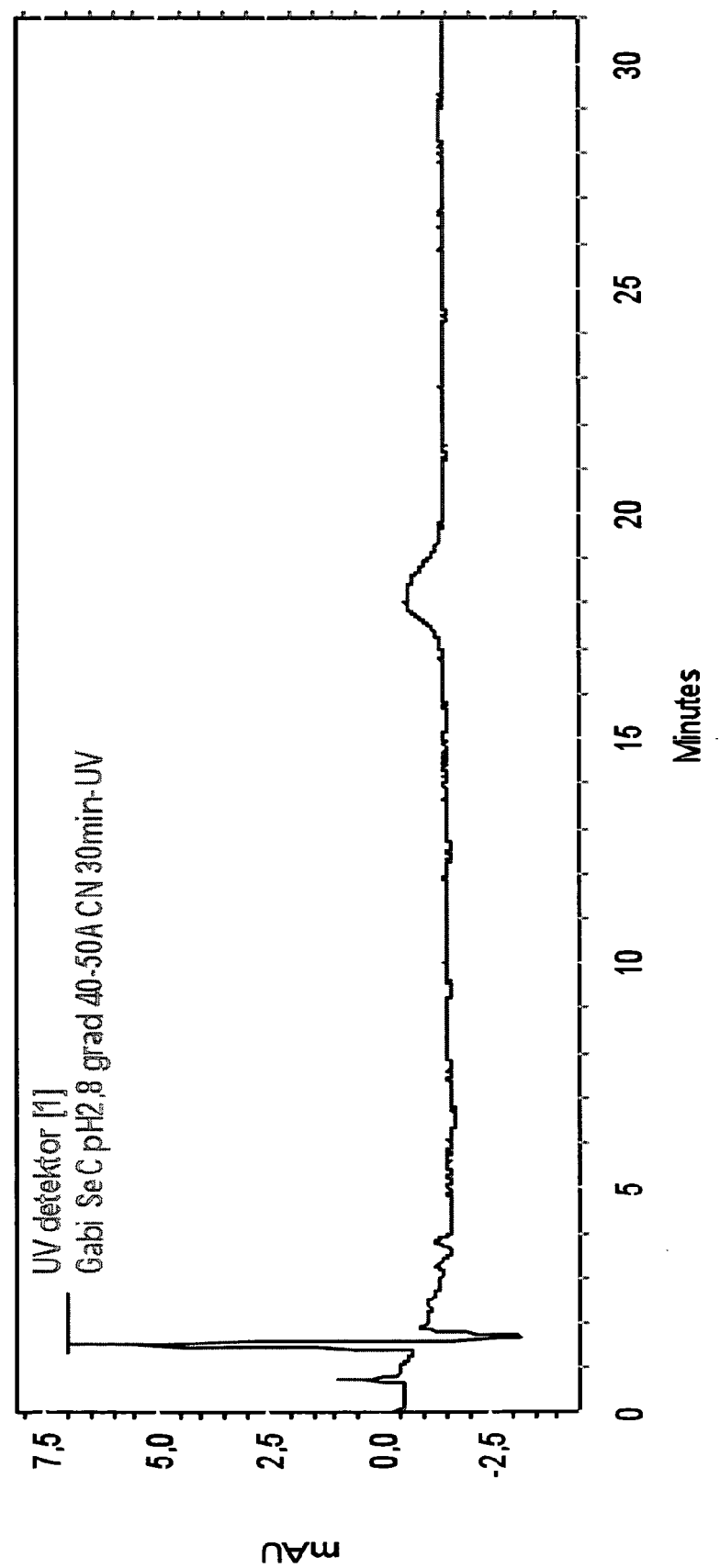

FIG. 7: RP-HPLC chromatogram (Knauer UV detector, =215 nm) of the reaction mixture of (PEG-Se)$_2$ reagent prepared from selenocystine. The signal at tr=18 min represents the absorbance of the polymer dimer Se—Se group, which shows that the synthesis of (PEG-Se)$_2$ proceeded in a quantitative yield.

FIG. 8: The SDS-PAGE analysis of G-CSF and (PEG-Se)$_2$ pegylation mixtures at pH 4.0, 5.0, 6.0, 7.0 and 7.5 (Simply blue staining, non-reducing conditions).
Lane 1: Protein MW standard (2.5 kDa, 3.5 kDa, 6 kDa, 14.4 kDa, 21.5 kDa, 31.0 kDa, 36.5 kDa, 55.4 kDa, 66.3 kDa, 97.4 kDa, 116.3 kDa, 200 kDa)
Lane 2: G-CSF+Neulasta
Lane 3: The pegylation mixture at pH 4.0
Lane 4: The pegylation mixture at pH 5.0
Lane 5: The pegylation mixture at pH 6.0
Lane 6: The pegylation mixture at pH 7.0
Lane 7: The pegylation mixture at pH 7.5

High molecular weight spot corresponds to G-CSF conjugated with 20 kDa Se-PEG reagent and low molecular weight spot corresponds to native G-CSF. The position of G-CSF dimer is marked with an arrow.

The results show that Se-PEG reagent can be used at acidic conditions and that the conjugation yield is better at higher pH.

C) Reactions Carried Out

Example 1

Preparation of (PEG-Se)$_2$ Reagent from Selenocystine and 10 kDa PEG-NHS

Step 1. Solubilization of Selenocystine:
8.5 mg of selenocystine was dissolved in 101.6 l of 1 M KOH. The pH was adjusted to ~9.8 by addition of 1.017 ml of 0.2 M K$_2$B$_4$O$_7$.
Step 2. Coupling Reaction of PEG and Selenocystine:
924 mg (0.092 mmol) of 10 kDa PEG-NHS reagent was dissolved in 2 ml of 0.2 M Na-phosphate pH 8.5. To this solution 0.411 ml (0.0092 mmol) of dissolved selenocystine (Step 1) was added. The reaction was allowed to proceed at room temperature for 18 h.
Step 3. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 4 ml.

Example 2

Preparation of (PEG-Se)$_2$ Reagent from Selenocystine and 10 kDa PEG-NHS in Dry DMF Step 1. Coupling Reaction of PEG and Selenocystine:
3.3 mg (0.01 mmol) of selenocystine was suspended in 3 ml of dry DMF containing 69.1 mg (0.5 mmol) K$_2$CO$_3$. After 1 hour, 200 mg (0.02 mmol) of 10 kDa PEG-NHS reagent was added and the reaction mixture was left stirring for 5 days at room temperature under inert argon atmosphere. To this solution 10 ml of water was added and the mixture was left to stir for 1 more day (quenching of PEG-NHS reagent by hydrolysis).

Step 2. Removal of Low Molecular Mass Impurities:
The polymer mixture was filtered and the resulting filtrate was washed three times with dichloromethane. The combined organic phase was concentrated under reduced pressure and the polymer mixture was precipitated by dropwise addition of diethylether. After the centrifugation, the precipitate was dried under high vacuum for 12 h at room temperature.

Example 3

Preparation of (PEG-Se)$_2$ Reagent from Selenocystamine and 10 kDa PEG-NHS

Step 1. Preparation of Selenocystamine Stock Solution:
6.2 mg of selenocystamine was dissolved in 0.31 ml of 0.2 M Na-phosphate pH 8.5.

Step 2. Coupling Reaction of PEG and Selenocystamine:
939 mg (0.094 mmol) of 10 kDa PEG-NHS reagent was dissolved in 4.26 ml of 0.2 M Na-phosphate pH 8.5. To this solution 0.15 ml (0.0094 mmol) of dissolved selenocystamine (Step 1) was added. The reaction was allowed to proceed at room temperature for 18 h.

Step 3. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 4.775 ml.

Example 4

Preparation of (PEG-Se)$_2$ and PEG-SeSO$_3$ Reagent from Selenocystine and 20 kDa PEG-NHS Step 1. Solubilization of Selenocystine:
23.3 mg of selenocystine was dissolved in 140 l of 1M KOH. The pH was adjusted to ~9.9 by addition of 0.4 ml of 0.2 M K$_2$B$_4$O$_7$.

Step 2. Coupling Reaction of PEG and Selenocystine:
610 mg (0.03 mmol) of 20 kDa PEG-NHS reagent was dissolved in 2 ml of 0.2 M Na-phosphate pH 8.5. To this solution 27.5 l (0.003 mmol) of dissolved selenocystine (Step 1) was added. The reaction was allowed to proceed at room temperature for 18 h.

Step 3. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 13.6 ml.

Step 4. The Preparation of Sulfitolysis Reagent:
Sulfitolysis reagent was prepared by dissolving 0.315 g of Na$_2$SO$_3$ and 0.121 g of Na$_2$S$_4$O$_6$ in 1 ml of 1 M TRIS/HCl solution with pH 8.0 and diluted to 25 ml with water.

Step 5. The Sulfitolysis of (PEG-Se)$_2$ Reagent:
6.25 ml of sulfitolysis reagent was added (100× molar excess of sulfite toward diselenide group) to the 10.2 ml of (PEG-Se)$_2$ reagent (Step 3). The reaction was allowed to proceed at room temperature for 18 h.

Step 6. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 8.1 ml.

Example 5

Preparation (PEG-Se)$_2$ and PEG-SeSO$_3$ Reagent from selenocystamine and 20 kDa PEG-NHS Step 1. The Preparation of Selenocystamine Stock Solution:
12.4 mg of selenocystamine was dissolved in 0.341 ml of 0.2 M Na-phosphate pH 8.5.

Step 2. Coupling Reaction of PEG and Selenocystamine:
583 mg (0.03 mmol) of 20 kDa PEG-NHS reagent was dissolved in 1.906 ml of 0.2 M Na-phosphate pH 8.5. To this solution 27.5 l (0.003 mmol) of dissolved selenocystamine (Step 1) was added. The reaction was allowed to proceed at room temperature for 18 h.

Step 3. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 13.0 ml.

Step 4. Sulfitolysis of (PEG-Se)$_2$ Reagent:
6.25 ml of sulfitolysis reagent (Example 4, Step 4) was added (100× molar excess of sulfite toward diselenide group) to the 9.75 ml of (PEG-Se)$_2$ reagent (Step 3). The reaction was allowed to proceed at room temperature for 18 h.

Step 5. Removal of Low Molecular Mass Impurities:
Amicon Ultra-15 with 10 MWCO was used for ultrafiltration. The buffer was exchanged to 0.2 M Na-phosphate pH 7.5. The volume after buffer exchange was 9.0 ml.

Example 6

Preparation of (PEG-Se)$_2$ from Selenocystamine and 20 kDa PEG-NHS

Step 1. The Preparation of Selenocystamine Stock Solution:
22.2 mg of selenocystamine was dissolved in 1.48 ml of 0.1 M K$_2$B$_4$O$_7$ pH 8.0.

Step 2. Coupling Reaction of PEG and Selenocystamine:
321 mg (0.016 mmol) of 20 kDa PEG-NHS reagent was dissolved in 1.075 ml of 0.1 M K$_2$B$_4$O$_7$ pH 8.0. To this solution 0.114 (0.0054 mmol) of dissolved selenocystamine (Step 1) was added. The reaction was allowed to proceed at room temperature, protected from light, for 24 h.

Step 3. Removal of Low Molecular Mass Impurities and Isolation of Solid (Peg-Se)$_2$:
The pH of the reaction mixture was adjusted to 3.0 by addition of oxalic acid and diluted with water to final volume of 20 ml. The buffer solution was then extracted three times with dichloromethane. The combined organic fractions were dried with Na$_2$SO$_4$. The organic solution was concentrated via rotary evaporation and the (PEG-Se)$_2$ was precipitated by dropwise addition of diethylether. After the centrifugation, the precipitate was dried under high vacuum for 12 h at room temperature.

Example 7

Conjugation of G-CSF with (PEG-Se)$_2$ Reagent Prepared from Selenocystine and 10 kDa PEG-NHS Step 1. Pegylation of G-CSF at Cys 18:
In order to adjust pH of G-CSF solution to 7.5, 3.636 ml of 0.2 M Na-phosphate pH 8.5 was added to 11.2 ml of G-CSF (20 mg) bulk solution. After that 2.18 ml of (PEG-Se)$_2$ reagent, prepared from selenocystine (Example 1, Step 3) and 0.172 ml of 10% SDS was added. The pegylation reaction was allowed to proceed at room temperature, protected from light, for 24 h. The pegylation mixture was analyzed by SDS-PAGE.

Example 8

Preparation of G-CSF Conjugate with (PEG-Se)$_2$ Reagent Prepared from Selenocystamine and 10 kDa PEG-NHS Step 1. Pegylation of G-CSF at Cys 18:
In order to adjust pH G-CSF solution to 7.5, 3.246 ml of 0.2 M Na-phosphate pH 8.5 was added to 10.8 ml G-CSF (19.2 mg) bulk solution. After that 3.65 ml of 10 kDa (PEG-Se)$_2$ reagent, prepared from selenocystamine (Example 3, Step 3) and 0.2 ml of 10% SDS were added. The pegylation reaction was allowed to proceed at room temperature, protected from light, for 26 h.

Step 2. Termination of Pegylation:
The buffer was exchanged to 25 mM CH$_3$COOH/NaOH 3.8 using Sephadex G-25 column and diluted 1+1 with the same buffer. After that the sample was left for 18 h at 4° C. The pegylation mixture was analyzed by SDS-PAGE under non-reducing conditions.

Step 3. Isolation of G-CSF Pegylated at Cys18 by CEC
Fractions that contained G-CSF pegylated at Cys 18 were eluted between 63% and 71% of eluting buffer. The pooled fractions were analyzed by SDS-PAGE under reducing and non-reducing conditions.

Example 9

Preparation of G-CSF Conjugate with (PEG-Se)$_2$ Reagent Prepared from Selenocystamine and 20 kDa PEG-NHS Step 1. Pegylation of G-CSF at Cys 18:
In order to adjust the pH of G-CSF solution to 7.5, 0.462 ml of 0.2 M Na-phosphate pH 8.5 was added to 1.4 ml of G-CSF (2.5 mg) bulk solution. After that 2.6 ml of (PEG-Se)$_2$ reagent, prepared from selenocystamine (Example 5, Step 3) and 0.045 ml of 10% SDS was added. The pegylation reaction was allowed to proceed at room temperature, protected from light, for 24 h.

Step 2. Termination of Pegylation:
The buffer was exchanged to 25 mM CH$_3$COOH/NaOH 3.8 using Sephadex G-25 column and diluted 1+1 with the same buffer. After that the sample was left for 24 h at 4° C.

Step 3. Isolation of G-CSF Pegylated at Cys18 by CEC:
Fractions that contained G-CSF pegylated at Cys 18 were eluted between 63% and 67% of eluting buffer. The pooled fractions were analyzed by SDS-PAGE under reducing and non-reducing conditions.

Example 10

Preparation of G-CSF Conjugate with PEG-SeSO$_3$ Reagent Prepared from Selenocystamine and 20 kDa PEG-NHS Step 1. Pegylation of G-CSF at Cys 18:
In order to adjust pH of G-CSF solution to 7.5, 2.039 ml of 0.2 M Na-phosphate pH 8.5 was added to 6.179 ml G-CSF (11 mg) bulk solution. 7.92 ml of kDa PEG-SeSO$_3$ reagent, prepared from selenocystamine (Example 5, Step 5) and 0.163 ml of 10% SDS were added. The pegylation reaction was allowed to proceed at room temperature, protected from light, for 24 h.

Step 2. Termination of Pegylation:
The buffer was exchanged to 25 mM CH$_3$COOH/NaOH 3.8 using Sephadex G-column and diluted 1+1 with the same buffer. After that the sample was left for 24 h at 4° C.

Step 3. Isolation of G-CSF Pegylated at Cys18 by CEC:
Fractions that contained G-CSF pegylated at Cys 18 were eluted between 59% and 67% of eluting buffer. The pooled fractions were analyzed by SDS-PAGE under reducing and non-reducing conditions Example 11

Conjugation of G-CSF with (PEG-Se)$_2$ Reagent, Prepared from Selenocystamine and 20 kDa PEG-NHS, at Different pH Values Step 1. Pegylation of G-CSF at Cys 18 in a Buffer with pH 4.0, 5.0, 6.0, 7.0 and 7.5
Before pegylation of G-CSF with (PEG-Se)$_2$ reagent, the pH of G-CSF solutions (140 μl/0.25 mg of G-CSF) was adjusted to 4.0, 5.0, 6.0, 7.0 and 7.5 by addition of 0 μl, 4.1 μl, 6.6 μl, 15.3 μl, and 7.2 μl of 0.2 M Na-phosphate respectively. To achieve the same concentration of G-CSF in all samples, appropriate volume of H$_2$O was added. The G-CSF was pegylated with 10 molar excess of 20 kDa (PEG-Se)$_2$ reagent in the presence of 0.1% of SDS for 24 h, at room temperature and protected from light. The pegylation mixtures were analyzed by SDS-PAGE.

We claim:

1. A conjugate comprising a water-soluble polymer and a pharmaceutically active agent comprising a thiol group, wherein the water-soluble polymer is linked via a S—Se-bond to the pharmaceutically active agent.

2. The conjugate according to claim 1, having a structure in accordance with formula VII

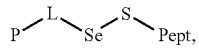

VII wherein P is a water-soluble polymer, L is a linking group, Se is a selenium atom, Pept is a polypeptide, and S is a sulfur atom belonging to a cysteine residue of the polypeptide.

3. A medicament comprising the conjugate according to claim 1.

4. A pharmaceutical composition comprising
   (a) a conjugate according to claim 1, and
   (b) one or more pharmaceutically acceptable excipients.

* * * * *